(12) United States Patent
Curry et al.

(10) Patent No.: US 10,894,101 B1
(45) Date of Patent: Jan. 19, 2021

(54) DISINFECTING DEVICE

(71) Applicant: Hydro LLC, Auburn, AL (US)

(72) Inventors: John Edgar Curry, Auburn, AL (US); Harry Edmar Schulz, Auburn, AL (US)

(73) Assignee: Hydro LLC, Auburn, AL (US)

( * ) Notice: Subject to any disclaimer, the term of this patent is extended or adjusted under 35 U.S.C. 154(b) by 0 days.

(21) Appl. No.: 16/900,243

(22) Filed: Jun. 12, 2020

(51) Int. Cl.
| A61L 2/10 | (2006.01) |
| A61L 2/08 | (2006.01) |
| A61L 2/18 | (2006.01) |
| A41D 31/06 | (2019.01) |
| A41D 27/20 | (2006.01) |

(52) U.S. Cl.
CPC .............. *A61L 2/084* (2013.01); *A41D 27/20* (2013.01); *A41D 31/065* (2019.02); *A61L 2/18* (2013.01); *A61L 2202/26* (2013.01)

(58) Field of Classification Search
CPC ....................................................... A61L 2/10
See application file for complete search history.

(56) References Cited

U.S. PATENT DOCUMENTS

| 3,619,336 | A | * | 11/1971 | Hughes | .................... D04H 1/52 428/91 |
| 2002/0146343 | A1 | | 10/2002 | Jenkins et al. | |
| 2007/0139930 | A1 | * | 6/2007 | Spivak | ................. A61N 5/0616 362/294 |
| 2011/0243789 | A1 | | 10/2011 | Roberts | |
| 2015/0257249 | A1 | * | 9/2015 | Kim | ......................... H05K 5/03 361/700 |
| 2016/0114067 | A1 | | 4/2016 | Dobrinsky et al. | |
| 2016/0317687 | A1 | * | 11/2016 | Dayton | ..................... A61L 2/10 |
| 2017/0128742 | A1 | * | 5/2017 | Rabiner | ............... A61N 5/0601 |
| 2018/0104367 | A1 | | 4/2018 | Bettles et al. | |
| 2020/0139152 | A1 | * | 5/2020 | Behler | ................. A61N 5/0621 |

FOREIGN PATENT DOCUMENTS

WO      2007010255 A1    1/2007

* cited by examiner

*Primary Examiner* — Donald R Spamer
(74) *Attorney, Agent, or Firm* — Bekiares Eliezer LLP (57) ABSTRACT

A device comprises a thermal reservoir, a light emitting diode (LED), a heat sink connecting the LED to the thermal reservoir and an insulating layer arranged on the thermal reservoir, the insulating layer including an orifice arranged over the LED such that light from the LED passes through the orifice in the insulating layer.

17 Claims, 11 Drawing Sheets

DISINFECTING DEVICE

BACKGROUND

The present invention relates to disinfecting surfaces, and more specifically, to disinfecting surfaces of hands.

Disinfecting hands is one of the most effective ways to avoid spreading contagious diseases. There are many methods used, to disinfect hands such as, soap and water, waterless soap, or solvent-based hand sanitizer. Each of these methods have disadvantages. For example, the use of soap and water is done at a fixed fixture such as a sink or hand washing station, the use of solvent-based hand sanitizers may be problematic since they are quickly depleted, and may not be available under some conditions.

A quick, effective, easily portable, and convenient device for sanitizing hands is desired.

SUMMARY

A device comprises a thermal reservoir, a light emitting diode (LED), a heat sink connecting the LED to the thermal reservoir and an insulating layer arranged on the thermal reservoir, the insulating layer including an orifice arranged over the LED such that light from the LED passes through the orifice in the insulating layer.

A garment comprising a pocket having a thermal reservoir, a light emitting diode (LED), a heat sink connecting the LED to the thermal reservoir; and an insulating layer arranged on the thermal reservoir, the insulating layer including an orifice arranged over the LED such that light from the LED passes through the orifice in the insulating layer.

A device comprising a thermal reservoir, a backing layer arranged on the thermal reservoir, a light emitting diode (LED), a heat sink connecting the LED to the thermal reservoir, an insulating layer arranged on the thermal reservoir, the insulating layer including an orifice arranged over the LED such that light from the LED passes through the orifice in the insulating layer, and a front layer arranged on the insulating layer the front layer includes a mesh portion arranged over the orifice.

DETAILED DESCRIPTION

As a preliminary matter, it will readily be understood by one having ordinary skill in the relevant art that the present disclosure has broad utility and application. As should be understood, any embodiment may incorporate only one or a plurality of the above-disclosed aspects of the disclosure and may further incorporate only one or a plurality of the above-disclosed features. Furthermore, any embodiment discussed and identified as being "preferred" is considered to be part of a best mode contemplated for carrying out the embodiments of the present disclosure. Other embodiments also may be discussed for additional illustrative purposes in providing a full and enabling disclosure. Moreover, many embodiments, such as adaptations, variations, modifications, and equivalent arrangements, will be implicitly disclosed by the embodiments described herein and fall within the scope of the present disclosure.

Accordingly, while embodiments are described herein in detail in relation to one or more embodiments, it is to be understood that this disclosure is illustrative and exemplary of the present disclosure, and are made merely for the purposes of providing a full and enabling disclosure. The detailed disclosure herein of one or more embodiments is not intended, nor is to be construed, to limit the scope of patent protection afforded in any claim of a patent issuing here from, which scope is to be defined by the claims and the equivalents thereof. It is not intended that the scope of patent protection be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection is to be defined by the issued claim(s) rather than the description set forth herein.

Additionally, it is important to note that each term used herein refers to that which an ordinary artisan would understand such term to mean based on the contextual use of such term herein. To the extent that the meaning of a term used herein—as understood by the ordinary artisan based on the contextual use of such term—differs in any way from any particular dictionary definition of such term, it is intended that the meaning of the term as understood by the ordinary artisan should prevail.

Regarding applicability of 35 U.S.C. § 112, ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. When used herein to join a list of items, "or" denotes "at least one of the items," but does not exclude a plurality of items of the list. Finally, when used herein to join a list of items, "and" denotes "all of the items of the list."

The following detailed description refers to the accompanying drawings. Wherever possible, the same reference numbers are used in the drawings and the following description to refer to the same or similar elements. While many embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the appended claims. The present disclosure contains headers. It should be understood that these headers are used as references and are not to be construed as limiting upon the subjected matter disclosed under the header.

The present disclosure includes many aspects and features. Moreover, while many aspects and features relate to, and are described in, the context of dispensing fluids, embodiments of the present disclosure are not limited to use only in this context. For example, the principles and techniques disclosed herein may be understood to be applicable for adaptively dispensing other kinds of substances based on associated characteristics.

As discussed above, a portable, quick and effective system for disinfecting hands is desired. In this regard, the use of ultraviolet (UV) lights may be employed to disinfect surfaces. Indeed, UV lights have been found to be effective in disinfecting hands and other services.

UV lights for disinfecting surfaces are often arranged in large fixtures or other devices. These are found in commercial or research settings for disinfecting foods and beverages, hospital rooms, or medical equipment. As discussed above, it is desirable for a system that disinfect hands while being portable and convenient.

The system and devices described herein includes a light emitting diode (LED) array that disinfects the surfaces of objects such as skin of the hands of the user. The device uses LEDs that emit ultraviolet light (and other light frequencies in some embodiments) that disinfects surfaces that it shines upon.

Previous UV disinfection devices were typically fixtures and not portable. Users would place the hands into a compartment with UV light for a period of time. Such a solution is not portable however, and is thus not convenient for most users. Described herein is an apparatus that is portable and emits ultraviolet light to disinfect the hands of the user while the user is undertaking their daily activities.

Figure 1:
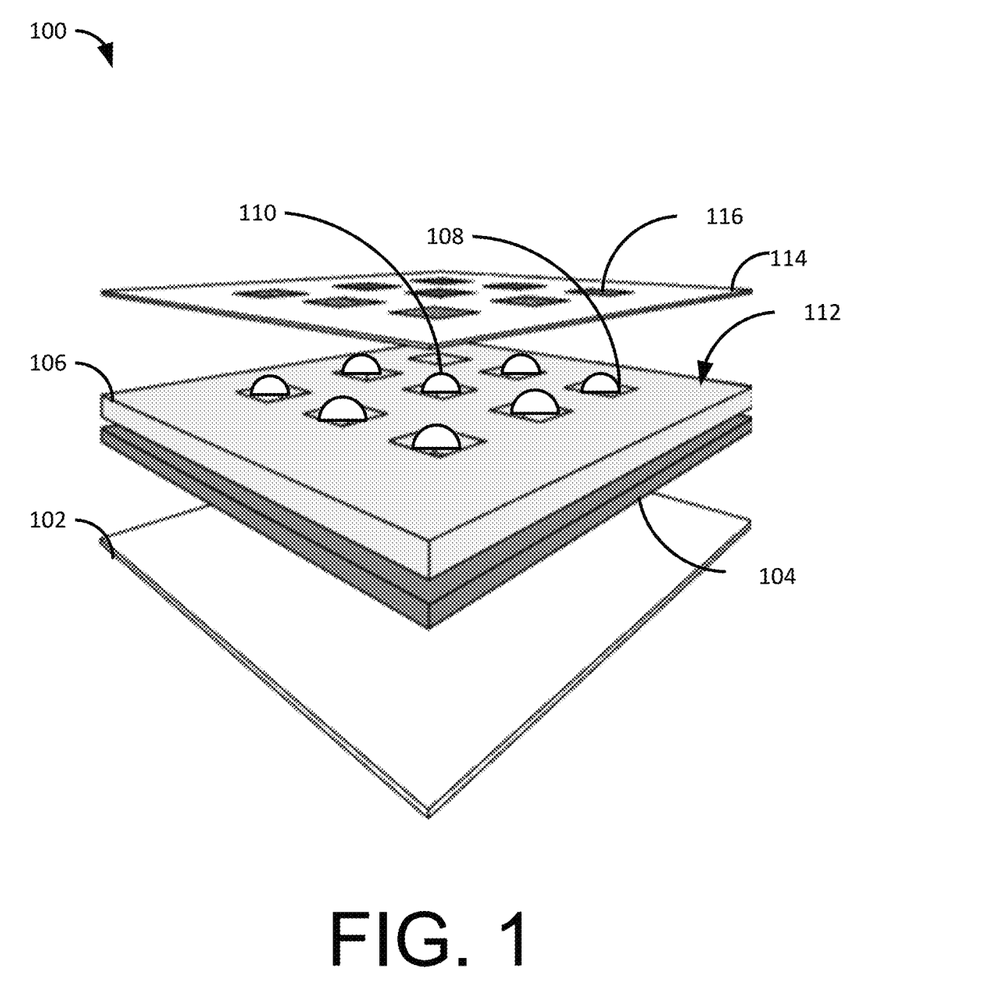
FIG. 1 illustrates an exploded planar view of a flexible disinfecting light device.

FIG. 1 illustrates an exploded planar view of a flexible disinfecting light device 100. The device 100 includes a backing cloth 102. The backing cloth 102 may include for example, any number of layers of material including, woven cloth, plastic sheet material, synthetic and natural fiber material. The backing 102 is attached to a thermal reservoir 104.

The thermal reservoir 104 is deformable, and may include any number of channels or cavities that contain a fluid that is operative to disperse heat. The thermal reservoir 104 is connected to the cloth 102 by, for example, stitching, an adhesive or welding process.

The thermal layer (insulating layer) 106 is connected to the thermal reservoir 104. Thermal layer 106 may include any suitable material such as, for example, neoprene or other similar materials that are flexible, deformable, and are resistant to heat. The thermal layer 106 includes a number of cavities 108. The cavities 108 expose LEDs (light emitting devices diodes 110). The LEDs 110 in the illustrated embodiment are shown as protruding from the surface 112 of the thermal layer. In other embodiments, the thermal layer 106 has a thickness that is greater than the height of the LEDs 110 such that the LEDs 110 do not protrude outwardly through the surface 112 of the thermal layer 106. The device 100 may include any number of LEDs 110.

The LEDs in the illustrated exemplary embodiment may output ultraviolet light or any other light incidental to outputting ultraviolet light. Other embodiments may output light at other wavelengths that has sanitizing or other therapeutic properties.

A top layer 114 is arranged on the thermal layer 112. The top layer 114 may be formed from any suitable sheet material such as a plastic woven fabric or any other type of suitable synthetic or natural material. The top sheet 114 has a number of orifices that are covered with screen material 116. The orifice generally correspond to the locations of the light emitting diodes 110. While the screen material 116 partially obscures the diodes so as to protect a user from touching warm LEDs 110 while allowing light to pass through the screens 116.

Each of the layers 102, 104, 106, and 114 may be connected together using any suitable method or methods, including for example stitching using adhesives or a welding process.

Figure 2:
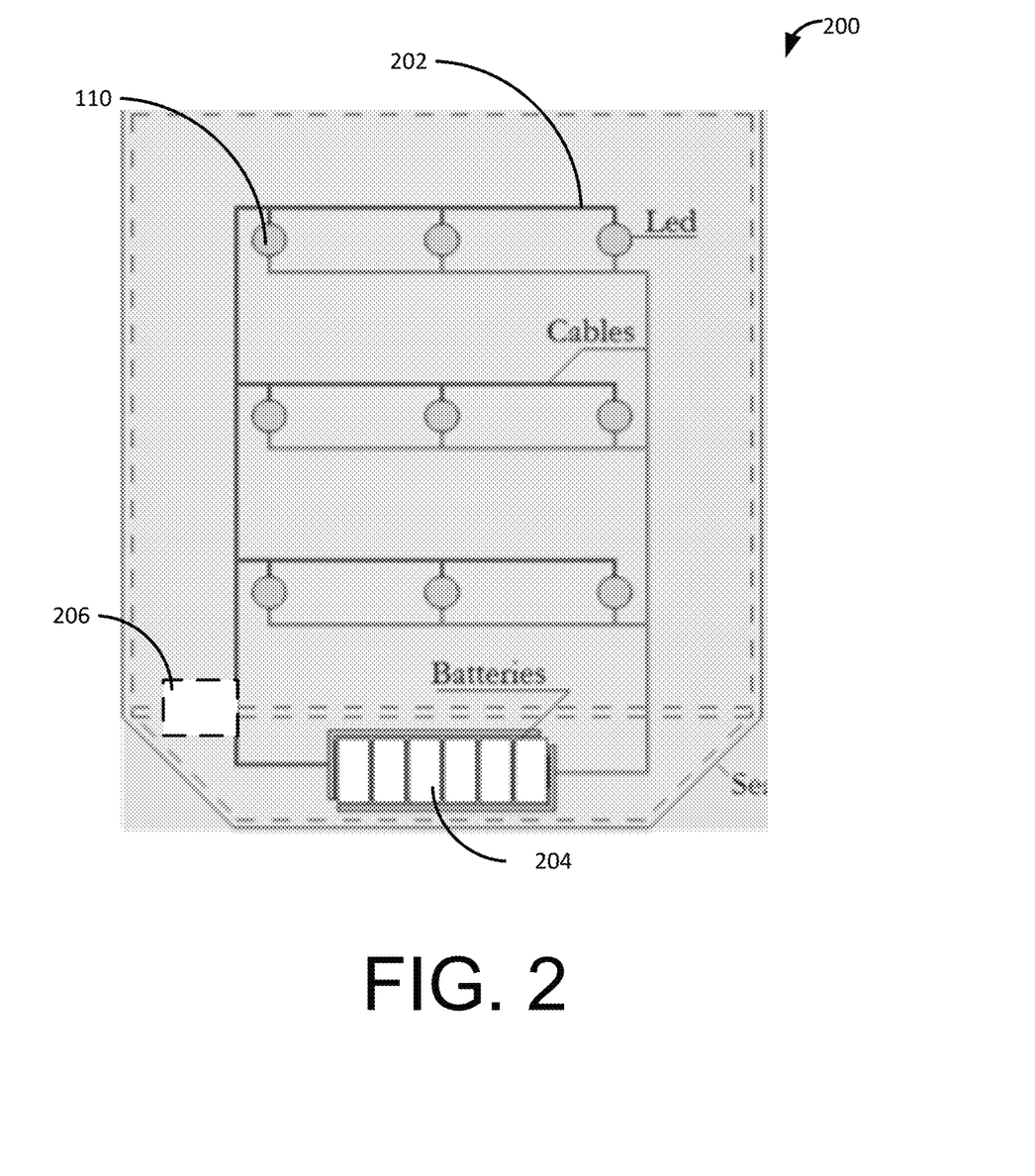
FIG. 2 illustrates a circuit.

FIG. 2 illustrates a circuit 200 that includes light emitting diodes 110 wires 202 and batteries 204 to form the circuit 200. The illustrated example embodiment, the circuit 200 is an "ideal circuit" alternative embodiments may include controllers and associated circuitry 206 and switches.

Figure 3:
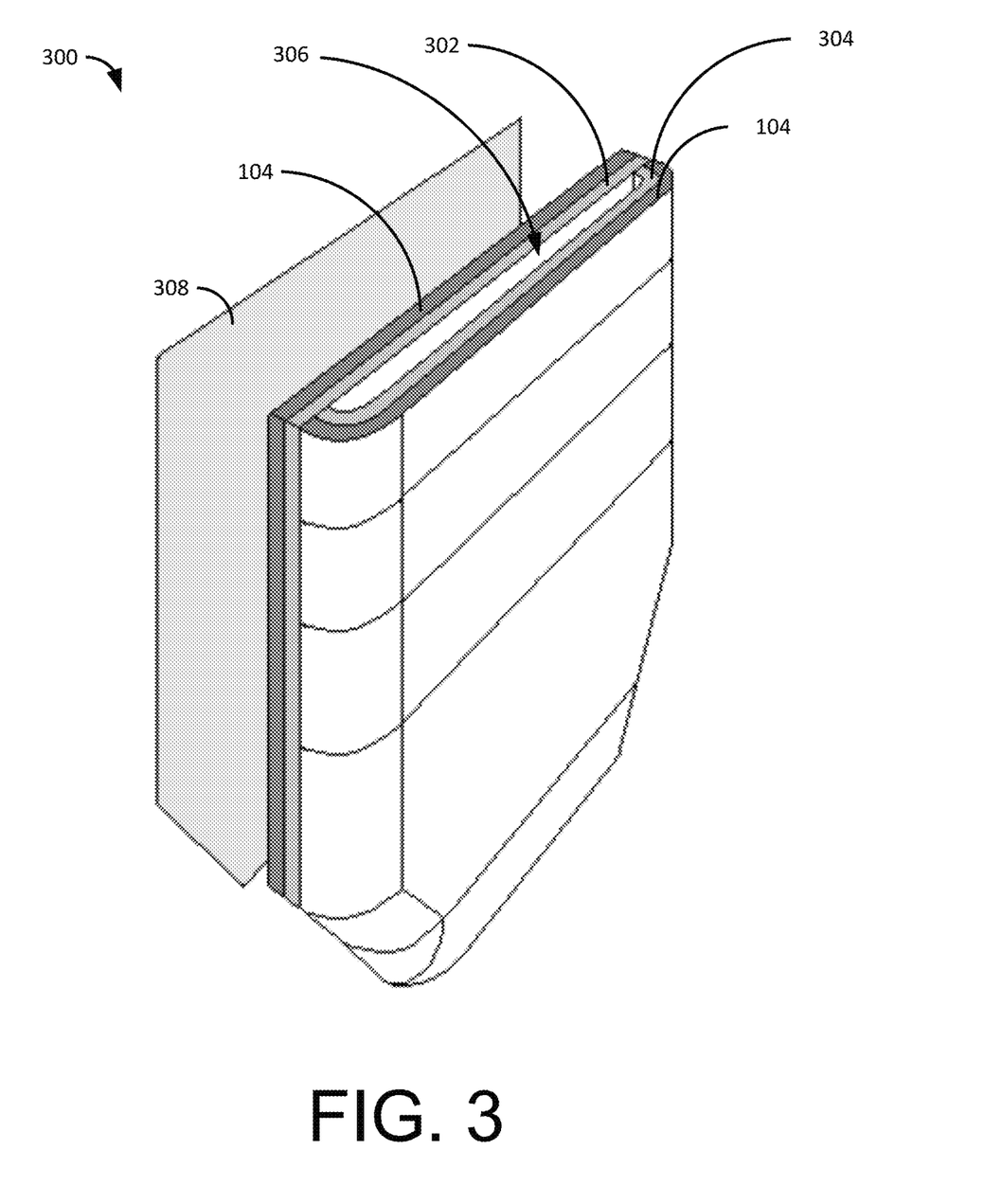
FIG. 3 illustrates a perspective view of an example embodiment of a pocket shaped disinfectant device.

FIG. 3 illustrates a perspective view of an example embodiment of a portion of a pocket shaped disinfectant device 300. The illustrated embodiment uses a first array 302 that is similar to the array 100 shown in FIG. 1, and array 304 is also similar to the array 100. The array 302 and 304 are arranged to define a pocket that has an inner cavity 306. A backing layer 308 may be attached to the device 300 to attach the device 300 to a garment or other suitable object.

The interior pocket 306 is lined with the top sheet 114 (of FIG. 1). The LEDs 110 shine through the screen material 112 (of FIG. 1) to illuminate the interior of the pocket and to direct ultraviolet light on opposing sides of the hand of the user.

Figure 4:
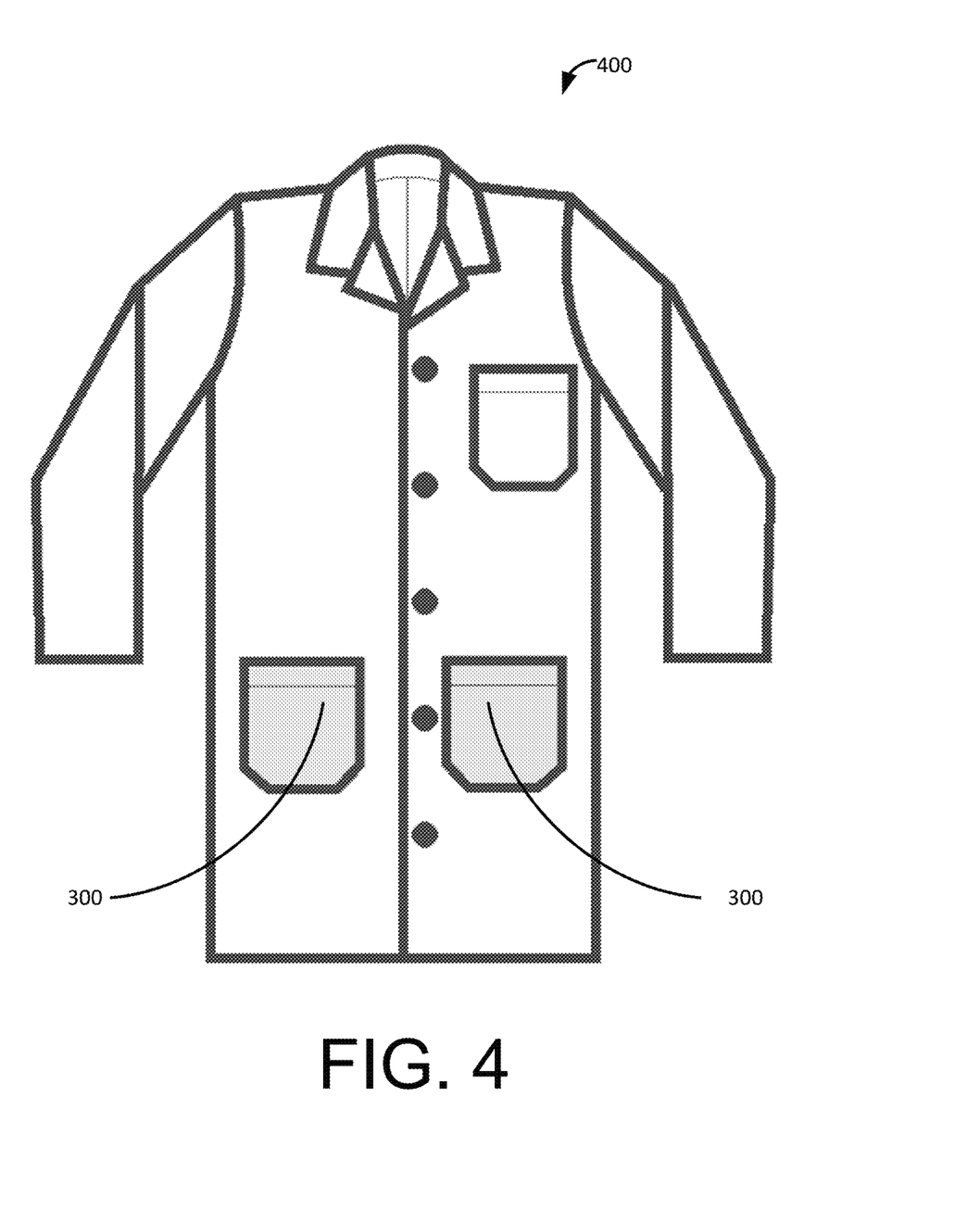
FIG. 4 illustrates a garment that includes the pocket.

FIG. 4 illustrates a garment 400 that includes the pocket 300. The pocket 300 may be attached to the garment 400 using, for example, hook and loop fasteners, snaps, buttons, or other suitable fasteners.

Figure 5:
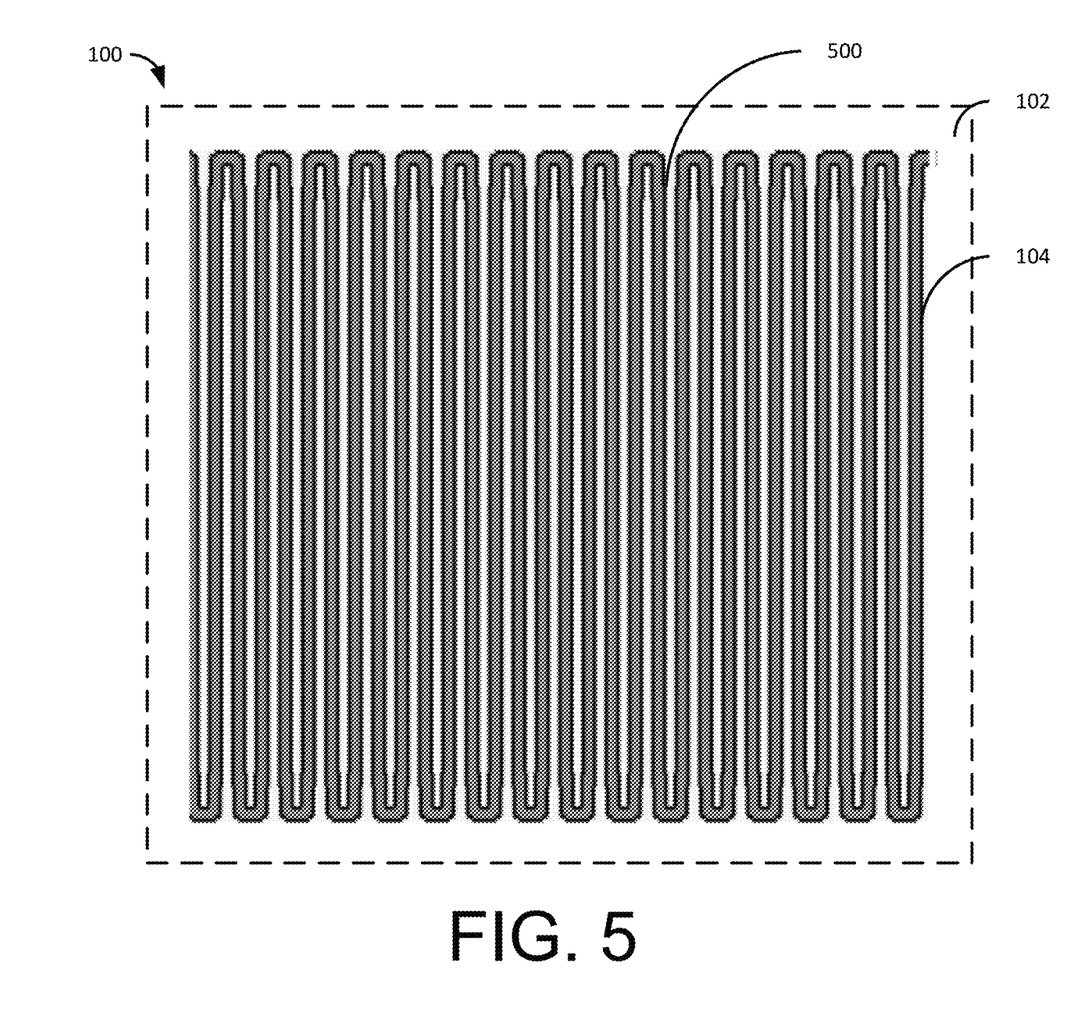
FIG. 5 illustrates the thermal reservoir attached to the backing sheet.

FIGS. 5-8 illustrate a method of manufacturing the device 100. FIG. 5 illustrates the thermal reservoir 104 attached to the backing sheet 102. The thermal reservoir in the illustrated embodiment includes a number of flexible tubes 500 that may be filled with a fluid, such as, for example, water, oil, or other fluid. The cooling channels 500 are operative to dissipate heat from the LEDs 110.

Figure 6:
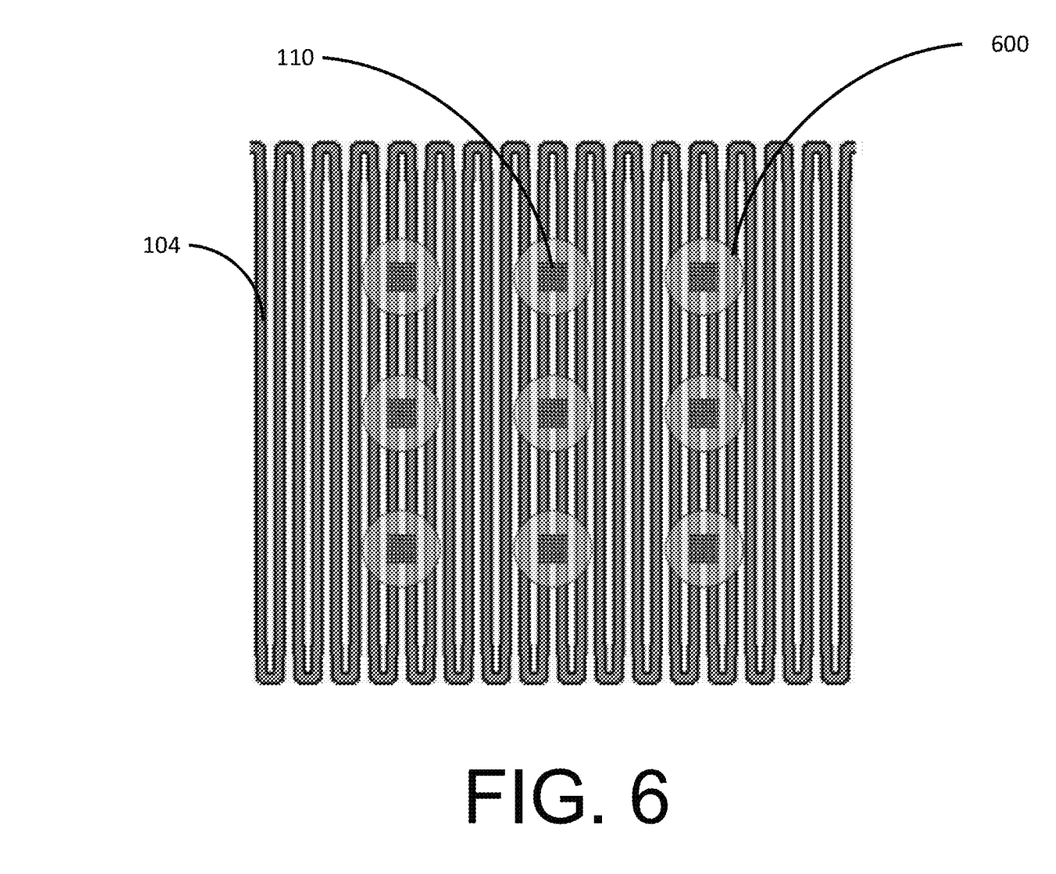
FIG. 6 illustrates a top view of the deposition of LEDs and heatsinks on the reservoir layer.

FIG. 6 illustrates a top view of the deposition of LEDs 110 and heatsinks 600 on the reservoir layer 104. LEDs 110 are connected to the thermal reservoir 104 by heatsinks 600. The heatsinks 600 are operative to conduct heat from the LEDs 110 to the thermal reservoir. The heatsinks 600 may be formed from any suitable material that conducts heat and is substantially flexible, such as, for example, a metallic material such as copper, aluminum, and silver. The heatsinks 600 may be arranged in any suitable shape such as a circular or spiral shape.

Figure 7:
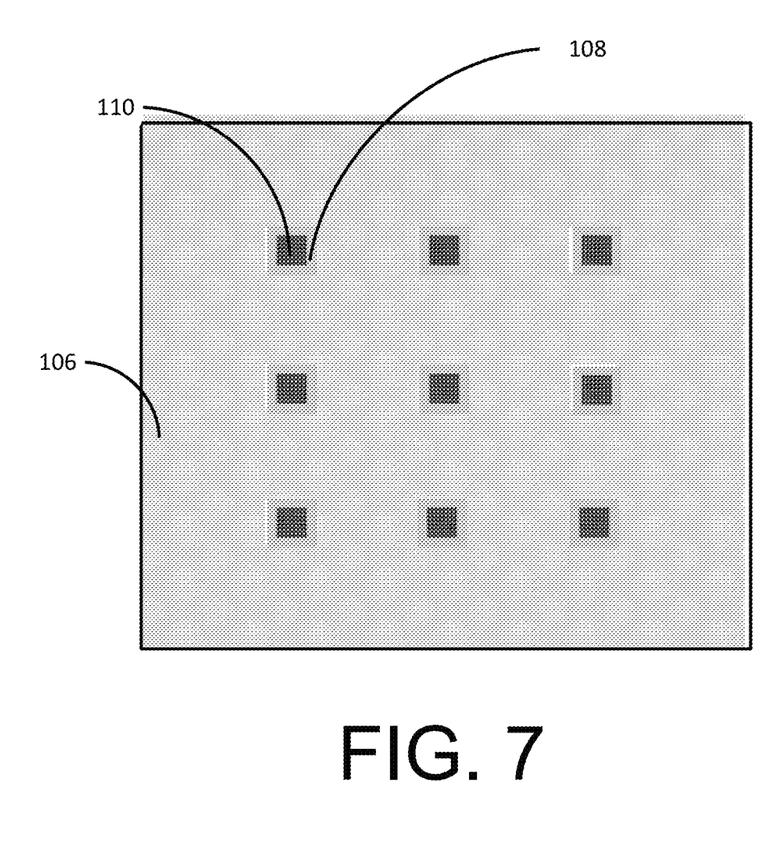
FIG. 7 illustrates top view of the resulting structure following the arrangement of the thermal (insulating) layer on the heat reservoir.

FIG. 7 illustrates a top view of the resulting structure following the arrangement of the thermal (insulating) layer 106 on the heat reservoir 104. Portions of the LEDs 110 are exposed via the orifices 108 in the thermal layer 106.

Figure 8:
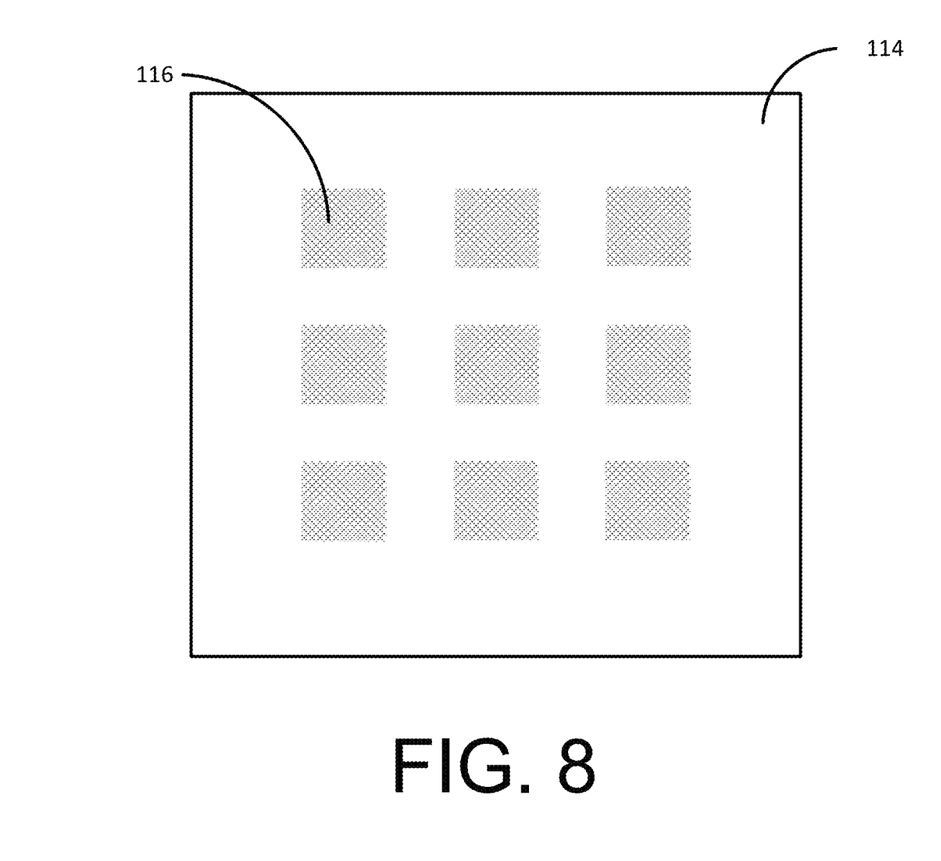
FIG. 8 illustrates top view of the resulting structure following application of the top layer.

FIG. 8 illustrates a top view of the resulting structure following the application of the top layer 114. The top layer 114 includes screens 116 which protect the user from touching warm LEDs 110 while allowing light to pass through the screens 116 to be emitted into the pocket.

Figure 9:
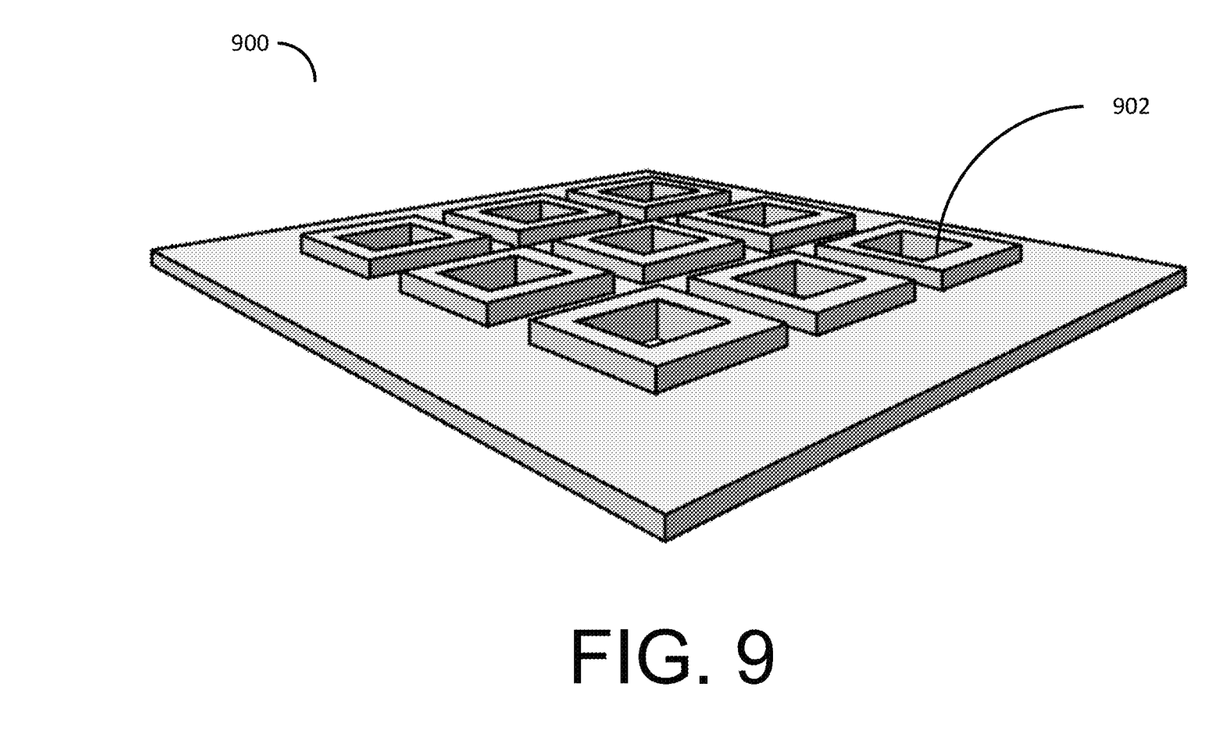
FIG. 9 illustrates a plan view of an alternate embodiment of a thermal layer.

FIG. 9 illustrates a plan view of an alternate embodiment of a thermal layer 900. The thermal layer 900 includes orifices one of the having raised rims 902.

Figures 10, 11, 12:
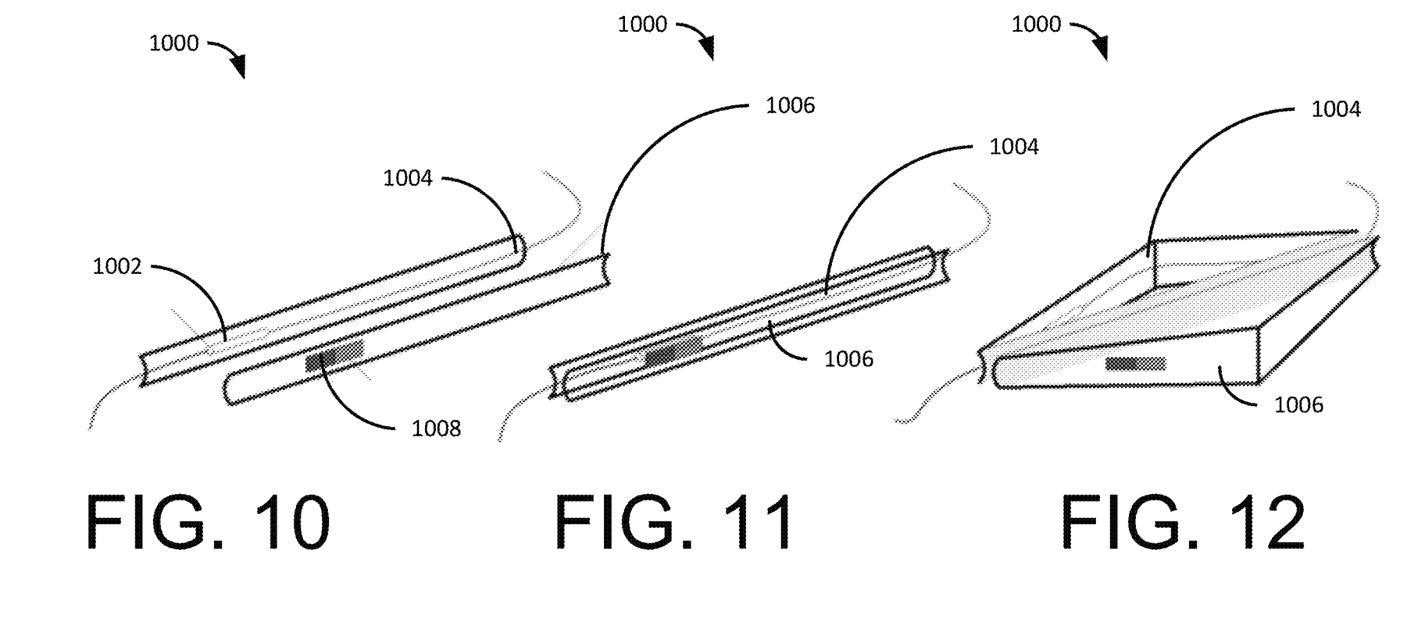
FIG. 10 shows a switch that is attached to a flexible elastic component.
FIG. 11 illustrates the arrangement of the flexible elastic components when set in a substantially parallel position.
FIG. 12 illustrates the flexing deformation of the flexible elastic components.

FIGS. 10-12 illustrate a perspective view of the operation of an example of a switch device 1000 that may be used to operate the pocket device 300 shown in FIG. 3 when placed on opposing sides of the pocket. The switch 1000 may be arranged proximate to the opening of the pocket such that the switch state is changed when an object such as, for example, a hand enters the pocket.

FIG. 10 shows a switch 1002 that is attached to a flexible and elastic component like a metal portion 1004. A magnet 1008 is attached to a second flexible and elastic component like a metal portion 1006.

FIG. 11 illustrates the arrangement of the flexible metal portions 1004 and 1006 when set in a substantially parallel position. The magnet 1008 is proximate to the reed switch 1002.

FIG. 12 illustrates the flexing deformation of the flexible components metal pieces 1004 and 1006. The deformation allows the hand of a user to enter into the pocket between the bent flexible components 1004 and 1006 while also separating the reed switch 1002 from the magnets 1008. In the illustrated example embodiment, when the switch 1002 is separated from the magnets 1008, such as when the hand of a user deforms the flexible components 1006, the LEDs 110 (of FIG. 1) illuminate the interior of the pocket and the contents of the pocket including the hands of the user.

Figure 13:
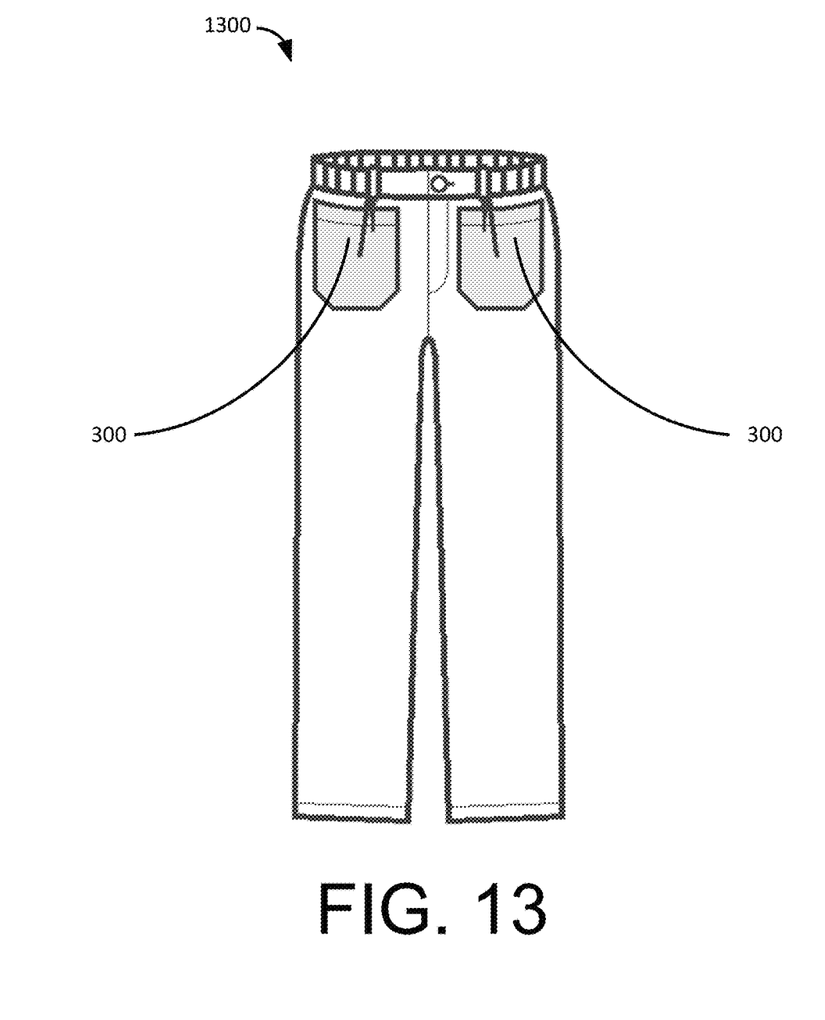
FIG. 13 illustrates an exemplary embodiment of a trouser garment.

FIG. 13 illustrates an exemplary embodiment of a trouser 1300 garment. The trousers 1300 includes features for receiving and retaining the device 300 such as, for example, hook and loop fasteners, snaps, buttons, or any other suitable attachment arrangement.

The embodiments described above include a method and device for disinfecting the hands of a user that may be worn as clothing. Such a device provides a pocket to receive and illuminate the hands of a user with a disinfecting light.

What is claimed is:

1. A device comprising:
   a thermal reservoir;
   a light emitting diode (LED);
   a heat sink connecting the LED to the thermal reservoir;
   an insulating layer arranged on the thermal reservoir, the insulating layer including an orifice arranged over the LED such that light from the LED passes through the orifice in the insulating layer; and
   a front layer arranged on the insulating layer, the front layer having a mesh portion arranged over the orifice.

2. The device of claim 1, further comprising a backing layer arranged on the thermal reservoir.

3. The device of claim 2, wherein the backing layer comprises a fabric.

4. The device of claim 1, wherein the LED is operative to emit a light that disinfects when shone on a surface.

5. The device of claim 1, wherein the thermal reservoir includes a liquid disposed in a channel.

6. The device of claim 1, further comprising a fastener layer arranged on a backing layer.

7. The device of claim 1, wherein the insulating layer is deformable.

8. The device of claim 1, wherein the thermal reservoir is deformable.

9. The device of claim 1, wherein the thermal reservoir and the insulating layer are connected by stitching.

10. The device of claim 1, wherein the device is actuated by a switch comprising:
   a first flexible portion;
   a second flexible portion; and
   the switch arranged on the first flexible portion, the switch operative to change states when the first flexible portion is separated from the second flexible portion.

11. The device of claim 1, arranged to form a pocket.

12. The device of claim 11, wherein the LED is arranged on a first portion of a pocket and a second LED is arranged on a second portion of the pocket that opposes the first portion of the pocket.

13. A garment comprising:
   a pocket having:
      a thermal reservoir;
      a light emitting diode (LED);
      a heat sink connecting the LED to the thermal reservoir;
      an insulating layer arranged on the thermal reservoir, the insulating layer including an orifice arranged over the LED such that light from the LED passes through the orifice in the insulating layer; and
      a front layer arranged on the insulating layer, the front layer having a mesh portion arranged over the orifice.

14. The garment of claim 13, further comprising a backing layer arranged on the thermal reservoir.

15. The garment of claim 13, wherein the LED is arranged on a first portion of the pocket and a second LED is arranged on a second portion of the pocket that opposes the first portion of the pocket.

16. The garment of claim 13, wherein the thermal reservoir is deformable.

17. A device comprising:
   a thermal reservoir;
   a backing layer arranged on the thermal reservoir;
   a light emitting diode (LED);
   a heat sink connecting the LED to the thermal reservoir;
   an insulating layer arranged on the thermal reservoir, the insulating layer including an orifice arranged over the LED such that light from the LED passes through the orifice in the insulating layer; and
   a front layer arranged on the insulating layer the front layer includes a mesh portion arranged over the orifice.

* * * * *